United States Patent [19]
Van Den Berg et al.

[11] Patent Number: 5,834,043
[45] Date of Patent: Nov. 10, 1998

[54] LACTOBACILLUS SAKE LIKE STRAINS, PRODUCTION AND USE OF THEIR EXOPOLYSACCHARIDES

[75] Inventors: Dirk Johannes Cornelis Van Den Berg, Delft; Adrianus Marinus Ledeboer, Rotterdam; Gerard Willem Robijn, Utrecht; Robert Vreeker, Melissant, all of Netherlands

[73] Assignee: Quest International B.V., Naarden, Netherlands

[21] Appl. No.: 446,831

[22] PCT Filed: Nov. 26, 1993

[86] PCT No.: PCT/EP93/03338

§ 371 Date: Sep. 19, 1995

§ 102(e) Date: Sep. 19, 1995

[87] PCT Pub. No.: WO94/12656

PCT Pub. Date: Jun. 9, 1994

[30] Foreign Application Priority Data

Dec. 2, 1992 [EP] European Pat. Off. .............. 92203728

[51] Int. Cl.$^6$ ................. A23C 9/12; A23G 3/00
[52] U.S. Cl. ................. 426/34; 426/42; 426/43; 426/61; 426/573; 426/580; 426/585; 426/602; 426/604; 426/605; 426/658; 435/101; 435/104; 435/252.9
[58] Field of Search .................. 426/61, 34, 36, 426/38, 42, 43, 658, 573, 574, 48, 49, 52, 580, 585, 601, 602, 604, 605; 435/101, 104, 252.9

[56] References Cited

U.S. PATENT DOCUMENTS 4,396,763 8/1983 Tsuchiya et al. ...................... 536/123
5,204,247 4/1993 Adachi et al. .......................... 435/101

FOREIGN PATENT DOCUMENTS 69-196521 8/1988 Japan .

OTHER PUBLICATIONS

H. Mizoguchi et al., "Separation of promotion factor on enzymic dissolution of rice from autolyzate of lactic acid bateria", Chemical Abstracts, 1991, vol. 115, No. 13, 1341841q, p. 805.

K. Higashi et al., "Nutritional requirement of hiochi bacteria under high ethanol concentration. VIII. Effect of ethanol on teichoic acid and polysaccharide in cell walls", Chemical Abstracts, 1989, vol. 110, No. 5, 36538k, p. 312.

J. Cerning et al., "Isolation and characterization of exocellular polysaccharide produced by *lactobacillus bulgaricus*", Chemical Abstracts, 1986, vol. 105, No. 23, 205849s, p. 322.

*Primary Examiner*—Leslie Wong
*Attorney, Agent, or Firm*—Young & Thompson

[57] ABSTRACT

New *Lactobacillus sake* like strains are provided obtainable from meat products, which strains are capable of producing an exopolysaccharide having shear-thinning properties, even at low concentrations, and/or thickening and/or emulsion-stabilizing properties.

17 Claims, 3 Drawing Sheets

LACTOBACILLUS SAKE LIKE STRAINS, PRODUCTION AND USE OF THEIR EXOPOLYSACCHARIDES

This is a 35 U.S.C. 371 national application of PCT/EP93,03338, filed Nov. 26, 1993.

BACKGROUND OF THE INVENTION

A large number of food products like mayonnaises, dressings, margarines, spreads or low-fat or zero-fat substitutes, can be stabilized by polysaccharides as emulsion stabilizers or thickening agents. Also in the medical, pharmaceutical and cosmetic fields, polysaccharides are used as emulsion stabilizers. Well known polysaccharides are obtained from a variety of plant seeds, e.g. guar gum from *Cyamopsis tetragonaloba* (guar), or locust bean gum (LBG) from locust bean. Other well known sources are seaweeds, giving carrageenan, alginates or agar.

One disadvantage of all these polysaccharides is, that the supply of the sources and thus the constant availability of the polysaccharides, is not certain, while demands are ever growing. This has already led to high and fluctuating prices for a highly functional polysaccharide like LBG. As an option to produce a product at reasonable prices the process described in EP-B-0121960 (UNILEVER) was developed for converting the cheaper, but less versatile polysaccharide guar gum into a clearly improved gum. A potentially commercial production of the required guar α-galactosidase was described in WO-A-87/07641 (UNILEVER)=U.S. Pat. No. 5,082,778.

Another disadvantage is that the isolation procedure for polysaccharides from seeds or seaweed is rather cumbersome.

A further disadvantage is that most of the polysaccharides have not the highly wanted, non-Newtonian property of shear-thinning, which is the effect that the viscosity reversibly decreases as the shear is enhanced, even at low concentrations.

A polysaccharide that both has the wanted shear-thinning property and is reliable with respect to production and isolation, is xanthan gum, a polysaccharide produced by the bacterium *Xanthomonas campestris* through fermentation. Consequently, xanthan gum is increasingly used in food and medical products and is expected to have by far the highest growth potential in the coming years. However, the producing microorganism, *Xanthomonas campestris,* is not food-grade. Moreover, a food product containing added xanthan gum has often to be labelled as containing an additive. This is disadvantageous in view of the present trends towards healthy "green" or only scarcely labelled food products.

Thus a need exists for a polysaccharide produced by a food-grade microorganism, having properties similar to or even superior to xanthan gum. Such a polysaccharide can either be added to the food product and the resulting product has to be labelled (but then the product is a so-called "friendly labelled" additive), or it can be produced in situ without the necessity of any labelling, because the microorganism is food-grade.

SUMMARY OF THE INVENTION

The present invention is based on the results of a large screening program involving about 600 lactic acid bacteria strains present in various food products, e.g. olives, traditional cheeses, and sour dough, which screening program resulted in the isolation of 30 exopolysaccharides-producing strains having thickening and/or emulsion-stabilizing properties. However, only some of these 30 lactobacilli, which appeared to be present in meat products, especially in Belgian sausages, produce exopolysaccharides (EPS) having (1) thickening and/or (2) emulsion stabilizing properties and/or even show (3) the highly desirable shear-thinning property, in particular at low concentrations. As an example thereof a Lactobacillus strain was isolated, characterised as a *Lactobacillus sake* like strain and given the name *Lactobacillus sake* like strain O-1. This strain, combining the three different properties mentioned above, was deposited under the conditions of the Budapest Treaty at the Centraalbureau voor Schimmelcultures in Baarn, The Netherlands with number CBS 532.92.

The present invention relates to an EPS obtainable from said *Lactobacillus sake* like strain O-1 as well as to exopolysaccharides obtainable from similar *Lactobacillus sake* like strains having either viscosity-increasing properties, or shear-thinning properties, or both. The EPS obtainable from *Lactobacillus sake* like strain O-1 comprises units of the monosaccharides rhamnose and glucose.

The invention also relates to a *Lactobacillus sake* like strain capable of producing such EPS. A preferred strain is the *Lactobacillus sake* like strain O-1, deposited as CBS 532.92.

The invention further relates to a process for producing such EPS comprising (a) growing a *Lactobacillus sake* like strain capable of forming an EPS in a suitable medium under conditions whereby said EPS is formed, and optionally (b) isolating the EPS formed. In one embodiment of this aspect of the invention such process can be used for the production of an EPS or an EPS-containing product, either of which can be used as an additive for food products or in medical, pharmaceutical and cosmetic applications. In another embodiment the process can be used for in situ production of an EPS comprising growing a *Lactobacillus sake* like strain in a dairy liquid medium under conditions whereby said EPS is formed until the culture has a relative high density of said lactobacilli. Preferably the product obtained by said process is not thereafter subjected to an intensive shear treatment. Such culture containing an EPS can advantageously be incorporated into dairy ingredient-containing products such as dressings, margarine, mayonnaise, and spreads, and low-fat or zero-fat substitutes therefor.

Figure 3:
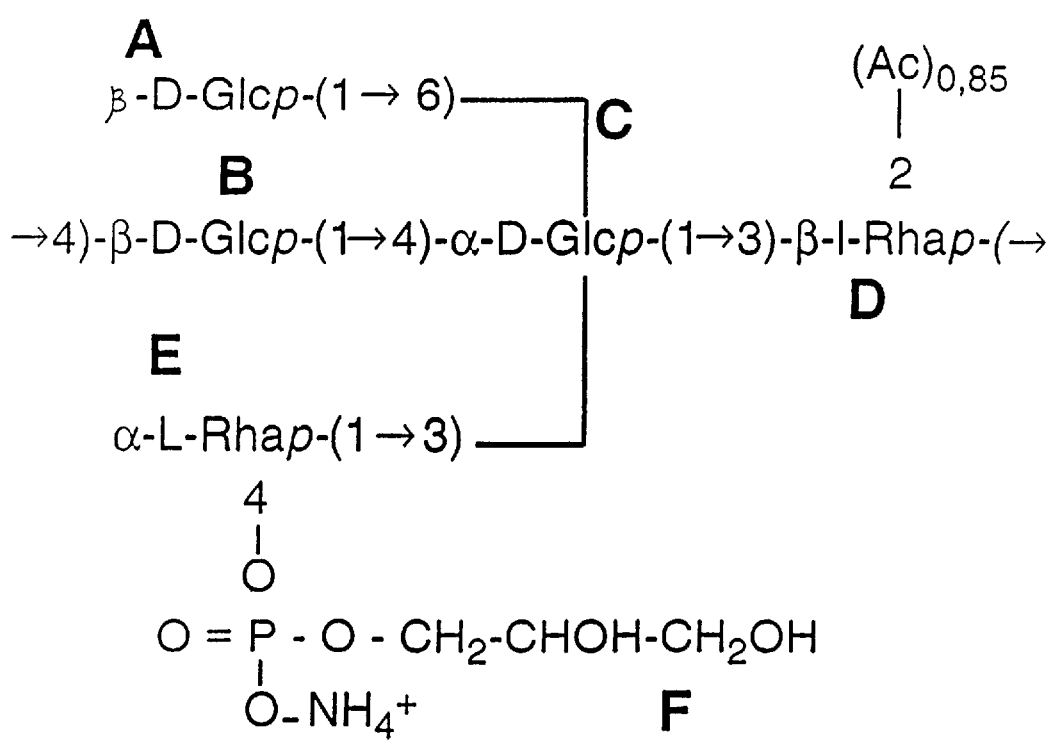

shear stress 1% O–1 EPS ▲▲ viscosity 1% O-1 EPS
▱▱ shear stress 1% xanthan ◆◆ viscosity 1% xanthan In FIG. 3 the structure of a preferred EPS according to the invention is provided.

DETAILED DESCRIPTION OF THE INVENTION

In one aspect the invention relates to a polysaccharide that can be produced by a *Lactobacillus sake* like strain, isolated from a meat product, e.g. a Belgian sausage. Thus the invention provides a polysaccharide obtainable from a food-grade *Lactobacillus sake* like strain. One preference is for a polysaccharide comprising units of the monosaccharides rhamnose and glucose, more preferably in a ratio of about 1:4 to about 1:1 most preferably in a ratio of 3:7 to 1:1.

It has been found that the EPS obtainable from *Lactobacillus sake* generally comprises acetyl and phospho glycerol side groups. The EPS is believed to be partially O-acylated, whereby the level of acylation is from 0.40 to 0.45 per rhamnose unit for example 0.425 per rhamnose unit. The level of phosphorylation is believed to be more than 0.45 per rhamnose unit, for example 0.50 per rhamnose unit. FIG. 3 gives the most likely structure as obtained by NMR techniques of the EPS obtained from *Lactobacillus sake* O-1. The EPS is composed of repeating pentasaccharide units with 3 glucose units and 2 rhamnose units, whereby one of the rhamnose units has a 1-phospho glycerol substituent and the other rhamnose unit contains on average about 0.85 O-acetyl groups.

For some embodiments of the invention it may be useful to reduce the number of substituent groups. This may be accomplished by conventional chemical techniques, for example the EPS may be O-deacylated by mild alkalic treatment, for example with ammonia. Also the EPS may be subjected to a highly alkaline treatment (NaOH) for further O-deacetylation and dephosphorylation. It is believed that removal of the side-groups may influence the rheology properties of the EPS.

Another preference is that the polysaccharide according to the invention gives a viscosity of at least 10 mPa.s when measured with a Haake Rotovisco RV100 viscosimeter at a concentration of 2 g/l (=0.2% wt.) in water and a shear rate of 300 $s^{-1}$, or a viscosity of at least 1000 Mpa.s when measured at a concentration of 10 g/l (=1% wt.) in water and a shear rate of 3 $s^{-1}$. Especially preferred is a viscosity of more than 100 Pa.s at a shear rate of 0.01 $s^{-1}$ and a concentration of 1 wt % in water.

Other preferred rheology characteristics of the EPS of the invention are: a value p of between 0.7 and 0.9, wherein the viscosity (Pa.s)≈(shear rate $(s^{-1})^{-p}$. Other characteristics are: viscosity of 1 wt % solution at 0.01 $s^{-1}$ is relatively T-independent (less than 50% fluctuation in the range 4° to 20° C.), pH independent (less than 10% fluctuation in pH range 4–6) and relatively independent on the presence of salts. Furthermore it has been observed that a synergistic increase in viscosity can be observed if the EPS of the invention is combined with guar gum or LBG. Also the EPS of the invention tend to act as a thickener rather than a gelling agent. This difference can be shown by shear modulus measurements.

Another preferred feature of a polysaccharide according to the invention is, that it has shear-thinning properties in that the viscosity is reversibly reduced upon increasing the shear rate. A most preferred polysaccharide is one that is obtainable from *Lactobacillus sake* like strain O-1 deposited as CBS 532.92. This latter polysaccharide has the following properties:

External appearance: tasteless and odourless white powder;

Solubility: readily soluble in water, scarcely soluble in methanol, ethanol and acetone;

Composition: 60–65% glucose units and 35–40% rhamnose units.

Viscosity: measured in an aqueous solution at 25° C. for both EPS from *Lactobacillus sake* like strain O-1 and xanthan as comparison

| | | viscosity in mPa.s | |
|---|---|---|---|
| concentration | shear rate | O-1 EPS | xanthan |
| 0.2% wt. | 300 $s^{-1}$ | 18 | 14 |
| 1.0% wt. | 3 $s^{-1}$ | 2440 | 1240 |

In another aspect the invention provides a process for producing a polysaccharide according to the invention, which process comprises (a) growing a *Lactobacillus sake* like strain capable of forming an EPS in a suitable medium under conditions whereby said EPS is formed, and optionally (b) isolating the EPS formed. A suitable medium appeared to be a so-called Semi Defined Medium (SDM) consisting of a carbon source like glucose or another fermentable carbohydrate, at least one nitrogen source, a phosphate source, e.g. a mixture of $Na_2HPO_4$ and $KH_2PO_4$ in such a concentration that it also has a high buffering capacity, vitamins, minerals (especially $Mn^{2+}$), amino acids and peptide mixtures. Two SDM's are given in Examples 1 and 6. As will be apparent to a skilled person these SDM's for laboratory trials need to be adapted when commercially producing the EPS at a larger scale. The strain is generally grown between 15° C. and 40° C. for 24 to 48 hours, without aeration for optimal production of the EPS. The EPS can be isolated from the fermentation broth by any suitable technique e.g. by means of a precipitation process using an organic solvent in which the EPS is not soluble or has a limited solubility. Another possibility is removal of the water, e.g. by evaporation, as is often done in the production of xanthan gum on a commercial scale, or by membrane filtration.

The thus isolated polysaccharide can be applied as such as an additive to food products. For convenience and easy handling, it is however sometimes preferred to apply the polysaccharide to a carrier material. This can be accomplished by any suitable technique. Any edible carrier material can be used, although the use of protein carriers e.g. whey protein or soy protein is especially preferred.

The polysaccharide can be applied as a "friendly" labelled additive in the production of dressings, mayonnaise, spreads and their low-fat and zero-fat equivalents, creams, sauces, meat (products) cheese, puddings, ice-cream and bakery products, using processes familiar to those skilled in the art, which will be further illustrated in the Examples. The level of polysaccharide will generally be from 0.01 to 15 wt %, more preferred 0.1 to 10 wt %, most preferred 0.5 to 5 wt %.

For some of these applications (e.g. cheese) it is preferred that the product is prepared under relatively quiescent conditions, e.g. gentle or no stirring after mixing the ingredients in order to avoid undesired shear-thinning.

Thus the invention also provides a process for producing a food product containing a thickened aqueous phase, which process comprises incorporating into said food product an effective amount of a polysaccharide according to the invention.

Another embodiment of this aspect of the invention which does not require labelling the food product as containing an additive, is a process in which the EPS is formed by the *Lactobacillus sake* like strain during fermentation of a commercially acceptable medium for starter cultures, after which the water can be removed by conventional techniques, e.g. evaporation, membrane filtration, or spray-drying.

Labelling is also not required when the polysaccharide is produced in situ by a food-grade micro-organism. An example is a process for producing a mayonnaise type product, in which milk or a milk-based medium, e.g. pasteurised skimmilk containing Hysoy (ex Quest Bioproducts, U.S.A.) and $MnSO_4$, is fermented with the *Lactobacillus sake* like strain at 30° C. for 18 hours until a sufficient high amount of lactobacilli is formed producing sufficient EPS. Subsequently the fermented milk product is carefully mixed both with an aqueous phase containing usual ingredients, e.g. salt, sugar, acids, flavour components and starch, and with a separately prepared mayonnaise pre-emulsion phase.

Thus the invention also provides a process for in situ producing a polysaccharide according to the invention, comprising growing a *Lactobacillus sake* like strain in an edible medium e.g. a dairy liquid medium under conditions whereby said EPS is formed until the number of said lactobacilli is in the order of $10^7$ to $10^{11}$ per ml, preferably $10^9$ to $10^{10}$ per ml. Preferably the product obtained by said process is not subsequently subjected to an intensive shear treatment.

Another embodiment of this aspect of the invention is a process for producing a product containing a dairy ingredient such as dressings, margarine, mayonnaise, and spreads, and low-fat or zero-fat substitutes therefor, which comprises incorporating into said product a liquid dairy medium obtained by a process for in situ producing a polysaccharide according to the invention. The dairy ingredient can form the total aqueous phase or at least part of the aqueous phase of said product.

The invention is further illustrated by the following Examples, which do not limit the scope of the present invention. Percentage in the following Examples are expressed as wt. unless otherwise stated.

EXAMPLE 1

Search for exopolysaccharide-producing lactic acid bacteria present in sausages

From 5 different home-made, traditionally fermented, chourico sausages from the region of Alenteijo in Portugal and from a traditionally fermented salami sausage from Recogne in Belgium, 10 g of sausage was suspended in 90 ml of 0.85% NaCl solution using a stomacher model BA6021 (ex Seward Laboratory). These suspensions were diluted $10^{-2}$, $10^{-4}$ and $10^{-6}$ times in 0.85% NaCl and 0.1 ml of the respective dilutions was plated out on MRS-agar which contained 20 mg pimafucine (ex Duchefa) per 100 ml medium to prevent growth of yeasts or fungi. The plates were incubated anaerobically at 30° C. for 48 hours.

In total 159 lactic acid bacteria strains were isolated. All strains were selected for the production of EPS as follows. The individual strain was grown overnight in MRS-broth at 30° C. "EPS selection medium" (ESM), composed of 9% skimmilk powder (ex Frico Domo), 0.35% Yeast Extract (ex Difco), 0.35% Bacto Pepton (ex Difco) and 1% glucose was inoculated with 1% (v/v) of this overnight culture. After 24 hours incubation at 30° C., the milk-curd was checked for "ropiness". To this end 1 ml of the milk-curd was taken up in a 1 ml volumetric pipet. The pipet was emptied again and when drops falling from the tip of the pipet showed a slimy behaviour, this referred to EPS-production in the ESM. With this method 4 of the 159 lactic acid bacteria strains isolated turned out to be EPS producers. These 4 strains were all isolated from the Belgium salami, whereas no EPS-producing strains could be isolated from the Portuguese sausages investigated.

The viscosity produced by a 1% (v/v) inoculum of an overnight grown culture (in MRS broth) in a Semi Defined Medium (SDM-1) (containing 2.5 g $K_2HPO_4$, 3.0 g $KH_2PO_4$, 0.6 g $(NH_4)_2$-citrate, 1.0 g Na-acetate, 5.0 g casamino acids (ex Difco), 6.7 g Yeast Nitrogen Base (ex Difco) and as a carbon source 2% glucose) incubated 24 hours at 30° C. was measured with the Haake Rotovisco RV100; system CV100 (sensor system ZA-30) at a shear rate of 300 $s^{-1}$. The viscosity of the 4 strains isolated from the Belgium salami turned out to be approximately the same and ranged from 1.9 to 2.2 mPa.s. As a typical strain we have chosen the one showing the highest viscosity, produced when grown under the above mentioned conditions.

This strain was named Lactobacillus sake like strain O-1. In this specification the abbreviated forms "strain O-1" and "O-1" are also used.

EXAMPLE 2

Physiological and taxonomical analysis of the exopolysaccharide producing *Lactobacillus sake* like strain O-1

The investigated strain O-1 is gram-positive, catalase-negative, immotile, and has rod-shaped bacteria occurring in short chains of in between 1 to 5 cells when grown in MRS broth. This strain was able to ferment the following sugar substrates (determined with API 50 CHL): L-arabinose, ribose, galactose, D-glucose, D-fructose, D-mannose, N-acetyl glucosamine, esculin, salicin, cellobiose, lactose, and saccharose.

The taxonomical identification of the lactic acid bacteria isolated from the various fermented sausages as mentioned in Example 1 was carried out using polyacrylamide gel-electrophoresis of proteins. The strains were grown on MRS agar in Roux flasks at 30° C. for 24 hours. Roux flasks were inoculated from a 24 hours grown MRS broth culture. Whole cell protein extracts were prepared as described previously (Kiredjan, 1986). Cells were lysed by sonication using a Labsonic 2000 sonicator (ex B. Braun, Melsungen, Germany) with a needle probe tip (length 127 mm, diameter 4 mm) during 3 minutes in position "LOW" with 50 W output. Sodium dodecylsulphate polyacrylamide gel-electrophoresis was carried out using the procedure of Laemmli (1970), which was modified as described by Kiredjan (1986). Registration of the protein electrophoretic patterns, normalization of the densitometric traces, grouping of strains by the Pearson product moment correlation coefficient (r) and UPGMA (Unweighted Pair Group Method using Average linkage) cluster analysis were performed by the techniques described by Pot (1992), using the software package GELCOMPAR (version 2.0; L. Vauterin & P. Vauterin, commercially available at Applied Maths, Risquons-Toutstraat 38, B-8511 Kortrijk, Belgium).

Figure 1:
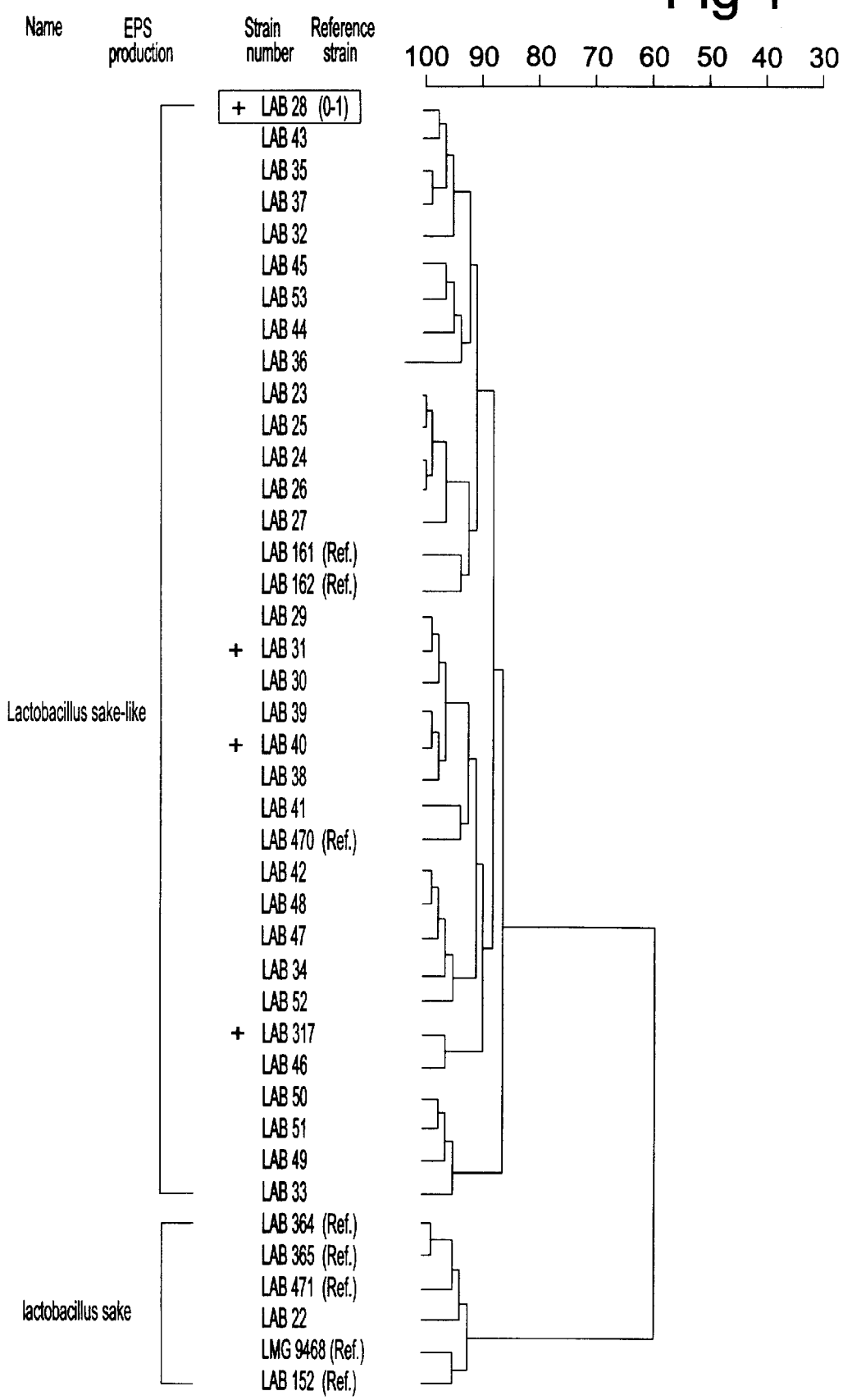
In FIG. 1 the UPGMA (Unweighted Pair Group Method using Average linkage) dendrogram of the Pearson Product Moment Correlation coefficients (r×100) between SDS-PAGE protein patterns is given. The strains assigned with a "LAB"-number are stored in the closed "Lactic Acid Bacteria" culture collection of the University of Ghent. Strains assigned with a "LMG"-number belong to the "Laboratorium voor Microbiologie, Gent" culture collections. The reference strains used in this study are indicated in the dendrogram, as are the EPS-producing strains. The strain "LAB28" (O-1) refers to the *Lactobacillus sake* like strain O-1 with deposit number CBS 532.92.

This method was used for the identification of 32 strains that were isolated from the traditionally fermented Belgium salami as mentioned in Example 1. Of these 32 strains 4 were able to produce EPS, one of which was the above indicated strain O-1. For the identification of these 32 strains the protein patterns were compared with the protein patterns of 600 lactic acid bacteria reference strains which were stored in a database. In FIG. 1 the UPGMA dendrogram of the mean correlation coefficient (r), calculated between all pairs of strains, is presented. Both the investigated strains and the closely related reference strains are indicated, clearly showing that the strains from the Belgium salami occupied a taxonomic position separate from the *Lactobacillus sake* reference strains. However, three reference strains which were phenotypically identified as *Lactobacillus sake* but showed aberrant protein patterns, were closely related to the strains isolated from the Belgian salami. These reference strains were known as "*Lactobacillus sake* like" and therefore the strains isolated from the Belgian salami were also considered to be "*Lactobacillus sake* like".

EXAMPLE 3

Isolation and purification of the exopolysaccharide produced by the *Lactobacillus sake* like strain O-1

A single colony of strain O-1 was selected from a MRS agar plate, transferred to fresh MRS broth and incubated overnight at 30° C. Freshly prepared Semi Defined Medium (SDM-1), as described in Example 1, was inoculated with 2.5% (v/v) of the overnight grown strain O-1 culture. This inoculated SDM-1 was incubated for 24 hours at 30° C. without aeration. To remove proteins from the culture broth trichloroacetic acid (TCA) was added until a concentration of 4% was reached. After gentle mixing the culture was allowed to stand for 30 minutes at room temperature. The culture was centrifuged for 30 minutes at 27000 g and the clear supernatant was collected. The EPS produced was precipitated with 2.5 volumes of cold ethanol. The precipitate was collected, redissolved in approximately 5% (v/v) of the original volume of water and dialysed against demineralized water for 2 days at 4° C. The water was refreshed twice a day. After dialysis a fractionated acetone precipitation was carried out. The bulk of the dissolved EPS was precipitated in the 50% (v/v) acetone fraction. This fraction contained about 80 wt.-% of the total amount of EPS and was 99 wt.-% pure, i.e. protein contamination<1 wt.-%. When an ≈100 wt.-% pure EPS is required the material can be further purified by gel filtration on a column of Sephacryl S-500 (ex Pharmacia). The precipitate of this Example was redissolved in demineralized water and lyophilized. The material was stored under dry conditions at 4° C.

EXAMPLE 4

Compositional analysis of the exopolysaccharide produced by the *Lactobacillus sake* like strain O-1

The sugar composition of the EPS produced by strain O-1 was determined. After methanolysis, followed by N-(re)acetylation and trimethylsilylation of the EPS the methyl glycosides of the different types of monosaccharides were determined by GC-MS. The EPS was composed of 60–70 wt.-% glucose and 30–40 wt.-% rhamnose.

EXAMPLE 5

Rheological behaviour of both the exopolysaccharide produced by the *Lactobacillus sake* like strain O-1 and xanthan gum produced by *Xanthomonas campestris*

Figure 2:
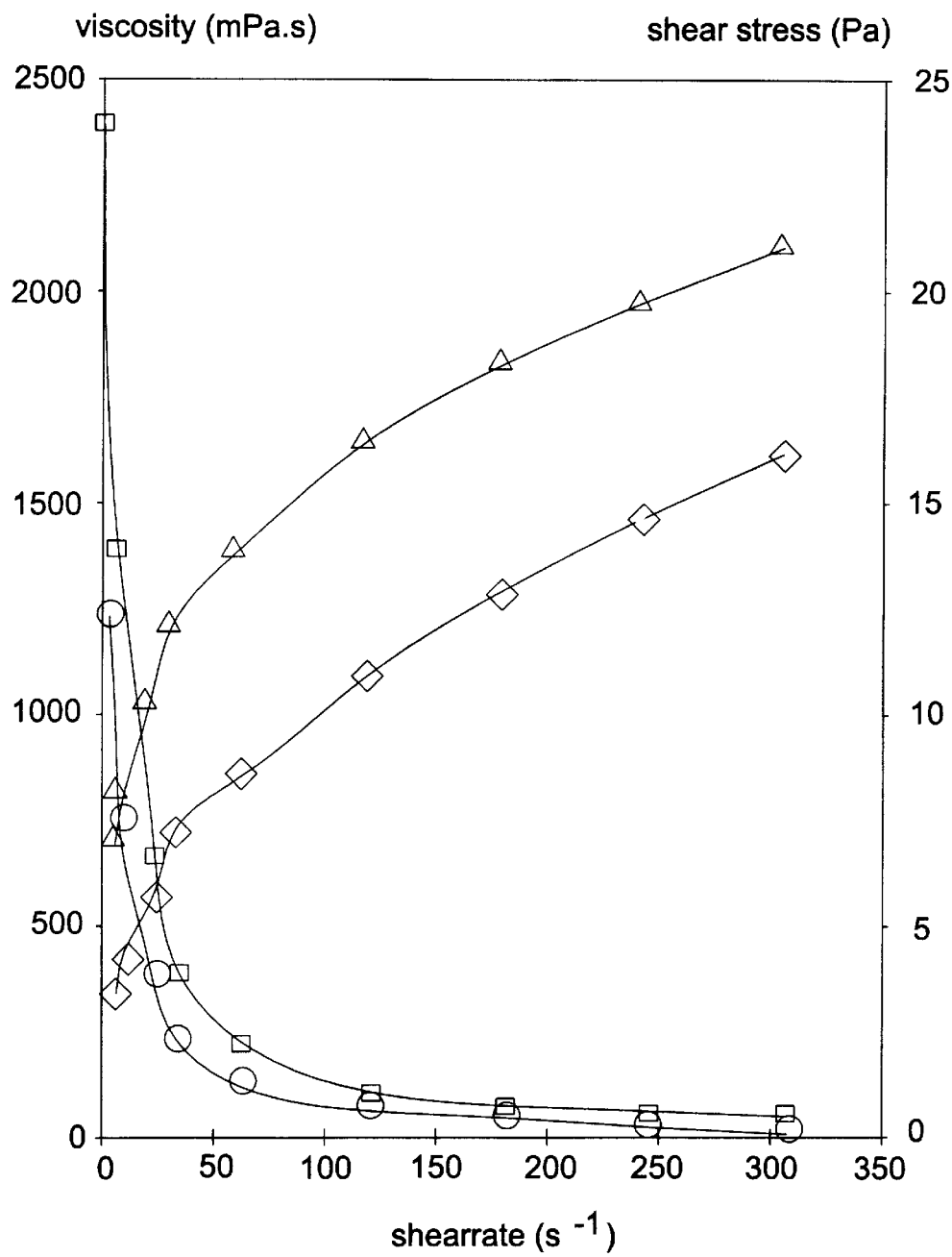
In FIG. 2 the shear rate versus viscosity and shear rate versus shear stress of a 1% (wt./vol.) aqueous solution of both the EPS from *Lactobacillus sake* like strain O-1 and xanthan gum are plotted.

The viscosity of a 1% aqueous solution of the EPS produced by strain O-1 was determined as a function of the shear rate. All rheological measurements were carried out at 25° C. using a Haake Rotovisco RV100; system CV100; sensor system ZA-30. In FIG. 2 the viscosity profile is compared with that of a 1% aqueous solution of xanthan gum (ex Kelco). In FIG. 2 it is clearly shown that the useful shear-thinning property of xanthan gum is also present in the O-1 EPS.

Detailed measurements at a shear rate of 3 $s^{-1}$, showed that the viscosity of a 1% aqueous solution of the O-1 EPS was 2440 mPa.s, where the viscosity of a 1% aqueous solution of xanthan gum was 1240 mPa.s. The viscosities measured at a shear rate of 300 $s^{-1}$ of a 1% aqueous solution of O-1 EPS and of xanthan gum were determined as 70 and 54 mPa.s respectively, whereas the viscosities measured at a shear rate of 300 $s^{-1}$ of a 0.2% aqueous solution of O-1 EPS and of xanthan gum were determined as 18 and 14 mPa.s, respectively.

EXAMPLE 6

Optimization of the growth of the exopolysaccharide producing *Lactobacillus sake* like strain O-1

In order to study the physiology of the production of EPS by strain O-1 a defined growth medium was desired. Since MRS is a rich, non-specified medium (containing yeast extract, beef extract etc.) and the medium used in Example 1 resulted in a poor growth (optical density at 610 nm was ≈1.2), a new Semi Defined Medium (SDM-2) was developed. For 1 liter SDM-2 the following components were weighed out: 10.0 g $K_2HPO_4$, 12.4 g $NaH_2PO_4$, 0.6 g $(NH_4)_2$-citrate, 0.05 g $MnSO_4$, 5.0 g casamino acids (ex Difco), 10.0 g Bacto proteose pepton (ex Difco), 6.7 g Yeast Nitrogen Base (ex Difco) and 20 g glucose. The final pH of the medium was 6.5. After incubation of strain O-1 in this SDM-2 at 35° C. in non-shaken Erlenmeyer flasks without pH control the $OD_{610}$ was 5.0, whereas growth in MRS resulted in a $OD_{610}$ of 3.5–4.0. Anaerobic incubation in SDM-2 at 20° C. for 48 hours resulted in a $OD_{610}$ of 6.5, whereas the viscosity of the culture broth was 3.8 mPA.s compared with a highest value of 2.2 when grown in SDM-1 (see Example 1). The concentration of the EPS in broth was 90 mg/l compared with a value of 30 mg/l when grown in SDM-1.

EXAMPLE 7

In situ production of the exopolysaccharide of *Lactobacillus sake* like strain O-1 in a milk-based medium 300 g milk powder and 30 g Hysoy (ex Quest Bioproducts, USA) were dissolved in water, up to an end volume of 3 l. It was pasteurised by incubating it for 1 minute at 90° C. Subsequently, 0.3 mM $MnSO_4$ was added and after cooling to about 30° C., the milk medium was inoculated with 1% (v/v) of an overnight culture of *Lactobacillus sake* like strain O-1, grown in the same medium. After incubating the culture for 18 hours at 30° C., a highly viscous fermented milk was obtained, which was used in the production of a low-fat dressing, as shown in the following Example.

EXAMPLE 8

Preparation of a dressing based on the in situ produced exopolysaccharide of *Lactobacillus sake* like strain O-1

A pre-emulsion phase was made by mixing equal volumes of vinegar and a mixture of water, egg-yolk, edible oil and B-carotene at low shear. This pre-emulsion phase was mixed with an aqueous phase containing sorbate, sugar, salt, vinegar, citric acid and instant starch and subsequently the mixture was homogenised at high shear. The exact composition of the mixtures depends on the properties, required for the final product. To this emulsion, the viscous fermented milk, the preparation of which was described in the preceding Example, was added at an end concentration of 10–20% (v/v). The mixture was carefully homogenised under low shear. A dressing having excellent body and taste was obtained.

EXAMPLE 9

A spread can be obtained by preparing an aqueous phase containing 2 wt % (on product) of the exopolysaccharide as described above and mixing 60 parts of the aqueous phase with 40 parts of a fat phase containing butterfat and 1% (on product) of monoglycerides.

EXAMPLE 10

Improved production of EPS

The following medium was used

| | |
|---|---|
| Na$_2$HPO$_4$ | 10 g/liter |
| KH$_2$PO$_4$ | 12 g/liter |
| (NH$_4$)$_2$-citrate | 0.6 g/liter |
| MnSO$_4$ | 0.05 g/liter |
| NZ-case Plus (exQuest) | 20 g/liter |
| glucose | 20 g/liter |
| Yeast nitrogen base (ex Difio) | 6.7 g/liter |
| pH (NaOH) | 5.8 |
| water | balance |

*Lactobacillus sake* O-1 was anaerobically grown on this medium at 20° C. while maintaining the pH at 5.8 for about 36 hours. Under these conditions 1350 mg EPS/l is produced. The structure of the EPS is determined by NMR and is as represented in FIG. 3 (ratio glucose: rhamnose 3:2, 0.425 O-acetyl groups per rhamnose unit, 0.5 1-phospho glycerol group rhamnose unit).

We claim:

1. Food grade exopolysaccharide obtainable from a food grade microorganism, said exopolysaccharide consisting of monosaccharide units rhamnose and glucose in the ratio of about 1:4–1:1 and possessing shear thinning properties in that the viscosity is reversibly reduced upon increasing the shear rates and possessing at least one of the properties of thickening and emulsion stabilizing.

2. Food grade exopolysaccharide according to claim 1 wherein rhamnose and glucose are in the ratio of 3:7–1:1.

3. Food grade exopolysaccharide according to claim 1 possessing repeating pentasaccharide units with 3 glucose and 2 rhamnose.

4. Food grade exopolysaccharide according to claim 1 possessing 60–65% glucose and 35–40% rhamnose.

5. Food grade exopolysaccharide according to claim 1, wherein said at least one property is thickening property.

6. Food grade exopolysaccharide according to claim 1, wherein said at least one property is emulsion stabilizing property.

7. Food grade exopolysaccharide according to claim 1 which possesses acetyl and phosphoglycerol side groups, being O-acylated at the rhamnose unit and phosphorylated at the rhamnose unit.

8. Food grade exopolysaccharide according to claim 1 wherein rhamnose is phosphorylated with a 1-phosphoglycerol substituent.

9. Food grade exopolysaccharide according to claim 1 with a viscosity of at least 10 mPA.s when measured with a viscosimeter in a concentration of 0.2 wt % in water and a shear rate of 300 s$^{-1}$ or of at least 1000 mPa.s when measured in concentration of 1 wt % in water and a shear rate of 3 s$^{-1}$ or of at least 100 Pa.s when measured in a concentration of 1 wt % in water at a shear rate of 0.01 s$^{-1}$.

10. Food grade exopolysaccharide according to claim 1 obtained from a microorganism strain with the phenotypical characteristics of *Lactobacillus sake* with aberrant protein patterns determinable from the UPGMA dendogram of the mean correlation coefficient (r).

11. Food grade exopolysaccharide according to claim 1 obtainable from *Lactobacillus sake*-like strain O-1 deposited at the Centraal Bureau voor Schimmelcultures in Baarn, the Netherlands under accession number CBS 532.92.

12. A *Lactobacillus sake*-like strain capable of producing an exopolysaccharide according to claim 1, said strain having the phenotypical characteristics of *Lactobacillus sake* with aberrant protein patterns determinable from the UPGMA dendogram of the mean correlation coefficient (r).

13. *Lactobacillus sake*-like strain according to claim 12, said strain being deposited at the Centraal Bureau voor Schimmelcultures in Baarn, the Netherlands under accession number 532.92.

14. A method for producing an exopolysaccharide according to claim 1 comprising growing a *Lactobacillus sake*-like strain in a suitable medium under conditions whereby the exopolysaccharide is formed and isolating the formed exopolysaccharide wherein suitable growing conditions comprise growth in a so-called semi-defined medium consisting of a carbon source, at least one nitrogen source, a phosphate source in such a concentration that it also has a high buffering capacity, vitamins, minerals, amino acids and peptide mixtures at a temperature between 15° C. and 40° C.

15. A process for in situ production of an exopolysaccharide according to claim 1 comprising growing a *Lactobacillus sake*-like strain according to claim 14 in an edible medium such as a dairy liquid under conditions whereby said EPS is formed until the number of Lactobacilli is in the order of 10$^7$–10$^{11}$ per ml.

16. A process for producing a food product containing a thickened aqueous phase, said process comprising incorporating into said food product an effective amount of a polysaccharide according to claim 1.

17. A process for producing a mayonnaise type product in which milk or a milk-based medium is fermented with a *Lactobacillus sake*-like strain according to claim 13 at 30° C. for 18 hours until a sufficient high amount of Lactobacilli is formed producing sufficient EPS followed by carefully mixing the fermented milk product with an aqueous phase containing usual ingredients and with a separately prepared mayonnaise preemulsion phase.

* * * * *